US009708611B2

(12) United States Patent
Mouradian et al.

(10) Patent No.: US 9,708,611 B2
(45) Date of Patent: Jul. 18, 2017

(54) RNA TARGETING IN ALPHA-SYNUCLEINOPATHIES

(71) Applicant: Rutgers, The State University of New Jersey, New Brunswick, NJ (US)

(72) Inventors: M. Maral Mouradian, Princeton, NJ (US); Eunsung Juun, East Brunswick, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 0 days.

(21) Appl. No.: 14/986,873

(22) Filed: Jan. 4, 2016

(65) Prior Publication Data
US 2016/0264965 A1 Sep. 15, 2016

Related U.S. Application Data

(63) Continuation of application No. 13/319,022, filed as application No. PCT/US2010/033896 on May 6, 2010, now Pat. No. 9,255,266.

(60) Provisional application No. 61/215,556, filed on May 6, 2009.

(51) Int. Cl.
*C12N 15/113* (2010.01)
*A61P 25/28* (2006.01)
*A61P 25/16* (2006.01)
*A61K 31/7105* (2006.01)

(52) U.S. Cl.
CPC ........ *C12N 15/113* (2013.01); *A61K 31/7105* (2013.01); *C12N 2310/141* (2013.01); *C12N 2310/321* (2013.01); *C12N 2320/30* (2013.01); *C12N 2320/32* (2013.01)

(58) Field of Classification Search
USPC ..... 424/450; 435/6.1, 91.1, 91.31, 320, 375, 435/455, 458; 514/44; 536/23.1, 24.5, 536/25.3
See application file for complete search history.

(56) References Cited

U.S. PATENT DOCUMENTS

| | | | |
|---|---|---|---|
| 7,232,806 | B2 | 6/2007 | Tuschl et al. |
| 2004/0219671 | A1 | 11/2004 | McSwiggen et al. |
| 2005/0185691 | A1 | 8/2005 | Slater |
| 2009/0004668 | A1 | 1/2009 | Chen et al. |

FOREIGN PATENT DOCUMENTS

| | | |
|---|---|---|
| WO | 0244321 A2 | 6/2002 |
| WO | 2006039253 A2 | 4/2006 |
| WO | 2007135426 A2 | 11/2007 |
| WO | 2008025073 A1 | 3/2008 |

OTHER PUBLICATIONS

Muramatsu, et al.: "A Phase I Study of Aromatic L-Amino Acid Decarboxylase Gene Therapy for Parkinson's Disease"; Sep. 2010, Molecular Therapy, vol. 18, No. 9, pp. 1731-1735.
Palfi, et al.: "Long-Term Safety and Tolerability of ProSavin, a Lentiviral Vector-Based Gene Therapy for Parkinson's Disease: A Dose Escalation, Open-Label, Phase 1/2 Trial"; Mar. 29, 2014, Lancet, vol. 383, pp. 1138-1146.
Mittermeyer, et al.: "Long-Term Evaluation of a Phase 1 Study of AADC Gene Therapy for Parkinson's Disease"; Apr. 2012, Human Gene Therapy, vol. 23, pp. 377-381.
Lewitt, et al.: "AAV2-GAD Gene Therapy for Advanced Parkinson's Disease; A Double-Blind, Sham-Surgery controlled, Randomised Trial"; Apr. 2011; Lancet Neurology, vol. 10, pp. 309-319.
Bartus, et al.: "Safety/Feasibility of Targeting the Substantia Nigra With AAV2-Neurturin in Parkinson Patients"; Neurology; 2013, vol. 80, pp. 1698-1701.
Valles, et al.; "Qualitative Imaging of Adeno-Associated Virus Serotype 2-Human Aromatic L-Amino Acid Decarboxylase Gene Therapy in a Phase I Study for the Treatment of Parkinson Disease"; Nov. 2010, Neurosurgery, vol. 67, pp. 1377-1385.
Kaplitt, et al.: "Safety and Tolerability of Gene Therapy with an Adeno-Associated Virus (AAV) Borne GAD Gene for Parkinson's Disease; An Open Label, Phase I Trial"; Jun. 23, 2007, Lancet, vol. 369, pp. 2097-2105.
Marks, Jr., et al.: "Safety and Tolerability of Initraputaminal Delivery of CERE-120 (Adeno-Associated Virus Serotype 2-Neurturin) to Patients with Idiopathic Parkinson's Disease: An Open-Label, Phase I Trial"; May 2008, Lancet Neurology, vol. 7, pp. 400-408.
Eberling, et al.: "Results form a Phase I Safety Trial of hAADC Gene Therapy for Parkinson Disease"; May 20, 2008, Neurology, vol. 70, pp. 1980-1983.
Christine, et al.: "Safety and Tolerability of Putaminal AADC Gene Therapy for Parkinson Disease", Nov. 17, 2009, Neurology, vol. 73, pp. 1662-1669.
Marks, Jr., et al.: "Gene-Delivery of AAV2-Neurturin for Parkinson's Disease: A Double-Blind, Randomised, Controlled Trial"; Dec. 2010, Lancet Neurology, vol. 9, pp. 1164-1172.
Zeng, et al.: "MicroRNA-2010 Overxpression Induces Angiogenesis and Neurogenesis in the Normal Adult Mouse Brain"; 2014, Gene Therapy, vol. 21, pp. 37-43.
Bushati, et al.: "MicroRNAs in Neurodegeneration"; 2008, Current Opinion in Neurobiology; vol. 18, pp. 292-296.
Vasudevan, et al.: "Switching from Repression to Activation: MicroRNAs Can Up-Regulate Translation"; Dec. 21, 2007, Science, vol. 318, pp. 1931-1934.
Agrawal, et al.: "Antisense Therapeutics: Is It as Simplel as Complementary Base Recognition?"; Feb. 2000, Molecular Medicine Today, vol. 6, pp. 72-81.
Crooke, S.T.: "Progress in Antisense Technology"; Annu. Rev. Medicine, 2004, vol. 55, pp. 61-95.
Chirila, et al.: "The Use of Synthetic Polymers for Delivery of Therapeutic Antisense Oligodeoxynucleotides"; Biomaterials, 2002, vol. 23, pp. 321-342.

(Continued)

*Primary Examiner* — Jane Zara
(74) *Attorney, Agent, or Firm* — Fox Rothschild LLP

(57) ABSTRACT

Therapies and assays to screen for small molecules that can have therapeutic use in the control of neurodegenerative diseases such as Parkinson's and other alpha-synucleinopathies.

9 Claims, 5 Drawing Sheets

(56) References Cited

OTHER PUBLICATIONS

Jang, et al.: "Gene Delivery from Polymer Scaffolds for Tissue Engineering"; Expert Rev. Medical Devices, 2004, vol. 1, No. 1, pp. 127-138.
Opalinska, et al.: "Nucleic-Acid Therapeutics: Basic Principles and Recent Applications"; Jul. 2002, Nature Reviews; vol. 1, pp. 503-514.
Peracchi, A: "Prospects for Antiviral Ribozymes and Deoxyribozymes"; 2004, Rev. Med. Virol, vol. 14, pp. 47-64.
Paroo, et al.: "Challenges for RNAi in Vivo"; Aug. 2004, Trends in Biotechnology; vol. 22, No. 8, pp. 390-394.
Doench, et al.: "Specificity of MicroRNA Target Selection in Translational Repression"; 2004, Genes & Development, vol. 18, No. 5, pp. 504-511.
Holen, et al.: "Positional Effects of Short Interfering RNAs Targeting the Human Coagulation Trigger Tissue Factor"; 2002, Nucleic Acids Research, vol. 30, No. 8, pp. 1757-1766.
Junn, et al.: "Repression of Alpha-Synuclein Expression and Toxicity by MicroRNA-7"; Aug. 4, 2009, Proceedings of the National Academy of Sciences of the United States of America, vol. 106, No. 31, pp. 13052-13057.
Anonymous; "Scientific Program of the 22nd Conference of the Hellenic Society for Neuroscience"; Oct. 16-19, 2008.
Nelson, et al.: "The mRNA of Alpha-Synuclein is a Putative MicroRNA (MIRNA) Target"; Jan. 1, 2003, Annual Meeting of the Society of Neuroscience, (Abstract Only).
Doxakis, E.: "Post-Transcriptional Regulation of Alpha-Synuclein Expression by MIR-7 and MIR-53"; Apr. 23, 2010, The Journal of Biological Chemistry, vol. 285, No. 17, pp. 1-14.

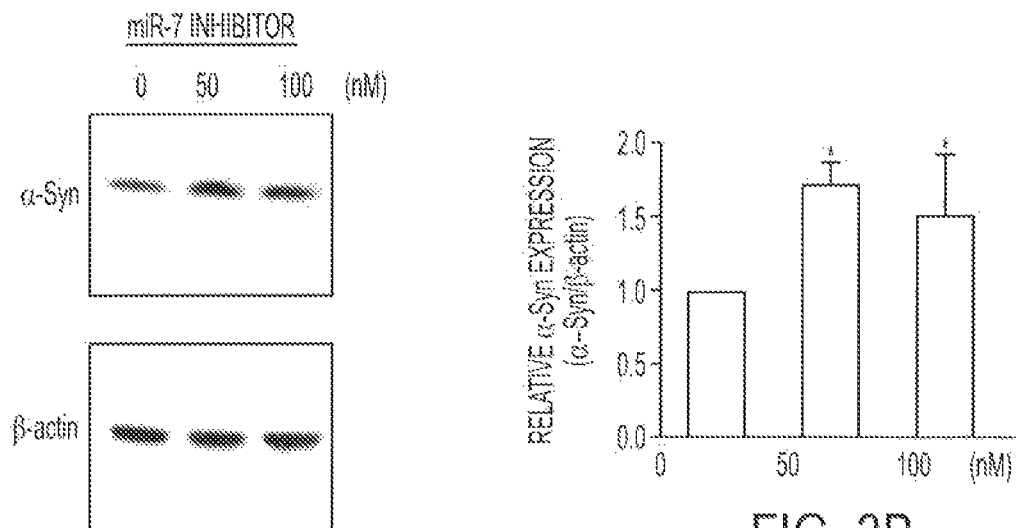
FIG. 3A
FIG. 3B
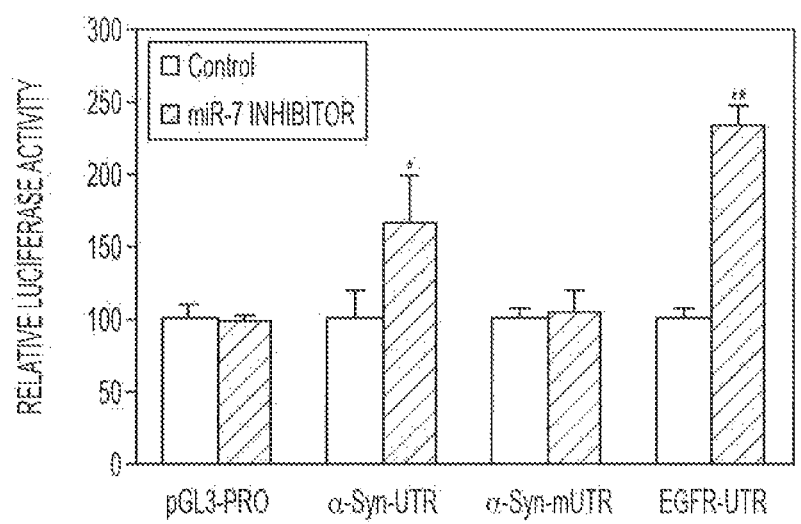
FIG. 3C

SEQUENCE LISTING

<160> NUMBER OF SEQ ID NOS: 36

<210> SEQ ID NO 1
<211> LENGTH: 23
<212> TYPE: RNA
<213> ORGANISM: Homo sapiens

<400> SEQUENCE: 1
uggaagacua gugauuugu ugu                                                  23

<210> SEQ ID NO 2
<211> LENGTH: 22
<212> TYPE: RNA
<213> ORGANISM: Homo sapiens

<400> SEQUENCE: 2
caacaaaucc cagucuaccu aa                                                  22

<210> SEQ ID NO 3
<211> LENGTH: 22
<212> TYPE: RNA
<213> ORGANISM: Homo sapiens

<400> SEQUENCE: 3 ucauuuugu gauguugcag cu                                                   22

<210> SEQ ID NO 4
<211> LENGTH: 22
<212> TYPE: RNA
<213> ORGANISM: Homo sapiens

<400> SEQUENCE: 4
uugcauaguc acaaaaguga uc                                                  22

<210> SEQ ID NO 5
<211> LENGTH: 22
<212> TYPE: RNA
<213> ORGANISM: Homo sapiens

<400> SEQUENCE: 5
cguguauuug acaagcugag uu                                                  22

<210> SEQ ID NO 6
<211> LENGTH: 22
<212> TYPE: RNA
<213> ORGANISM: Homo sapiens

<400> SEQUENCE: 6
ugucaguuug ucaaauaccc ca                                                  22

<210> SEQ ID NO 7
<211> LENGTH: 22
<212> TYPE: RNA
<213> ORGANISM: Homo sapiens

<400> SEQUENCE: 7
agacccuggu cugcacucua uc                                                  22

<210> SEQ ID NO 8
<211> LENGTH: 21
<212> TYPE: RNA
<213> ORGANISM: Homo sapiens

<400> SEQUENCE: 8

-continued gggagugcag ggcaggguuu c                                          21

<210> SEQ ID NO 9
<211> LENGTH: 20
<212> TYPE: RNA
<213> ORGANISM: Homo sapiens

<400> SEQUENCE: 9
ggggagcugu ggaagcagua                                            20

<210> SEQ ID NO 10
<211> LENGTH: 23
<212> TYPE: RNA
<213> ORGANISM: Homo sapiens

<400> SEQUENCE: 10
uaggcagugu cauuagcuga uug                                        23

<210> SEQ ID NO 11
<211> LENGTH: 22
<212> TYPE: RNA
<213> ORGANISM: Homo sapiens

<400> SEQUENCE: 11
caaucacuaa cuccacugcc au                                         22

<210> SEQ ID NO 12
<211> LENGTH: 22
<212> TYPE: RNA
<213> ORGANISM: Homo sapiens

<400> SEQUENCE: 12
uuauaauaca accugauaag ug                                         22

<210> SEQ ID NO 13
<211> LENGTH: 27
<212> TYPE: RNA
<213> ORGANISM: Homo sapiens

<400> SEQUENCE: 13
caauccuuau cagauuguau uguaauu                                    27

<210> SEQ ID NO 14
<211> LENGTH: 22
<212> TYPE: RNA
<213> ORGANISM: Homo sapiens

<400> SEQUENCE: 14
auauaauaca accugcuaag ug                                         22

<210> SEQ ID NO 15
<211> LENGTH: 22
<212> TYPE: RNA
<213> ORGANISM: Homo sapiens

<400> SEQUENCE: 15
cuuagcaggu uguauuauca uu                                         22

<210> SEQ ID NO 16
<211> LENGTH: 22
<212> TYPE: RNA
<213> ORGANISM: Homo sapiens -continued

```
<400> SEQUENCE: 16
auaauacaac cugcuaagug cu                                              22

<210> SEQ ID NO 17
<211> LENGTH: 22
<212> TYPE: RNA
<213> ORGANISM: Homo sapiens

<400> SEQUENCE: 17
cacuuagcag guuguauuau au                                              22

<210> SEQ ID NO 18
<211> LENGTH: 21
<212> TYPE: RNA
<213> ORGANISM: Homo sapiens

<400> SEQUENCE: 18
cuuuuugcgg ucugggcuug c                                               21

<210> SEQ ID NO 19
<211> LENGTH: 22
<212> TYPE: RNA
<213> ORGANISM: Homo sapiens

<400> SEQUENCE: 19
aagcccuuac cccaaaaagu au                                              22

<210> SEQ ID NO 20
<211> LENGTH: 22
<212> TYPE: RNA
<213> ORGANISM: Homo sapiens

<400> SEQUENCE: 20
aagcccuuac cccaaaaagc au                                              22

<210> SEQ ID NO 21
<211> LENGTH: 22
<212> TYPE: RNA
<213> ORGANISM: Homo sapiens

<400> SEQUENCE: 21
ggauaucauc auauacugua ag                                              22

<210> SEQ ID NO 22
<211> LENGTH: 20
<212> TYPE: RNA
<213> ORGANISM: Homo sapiens

<400> SEQUENCE: 22
uacaguauag augauguacu                                                 20

<210> SEQ ID NO 23
<211> LENGTH: 22
<212> TYPE: RNA
<213> ORGANISM: Homo sapiens

<400> SEQUENCE: 23
ggugcagugc ugcaucucug gu                                              22

<210> SEQ ID NO 24
<211> LENGTH: 21
<212> TYPE: RNA
<213> ORGANISM: Homo sapiens
```

-continued

```
<400> SEQUENCE: 24
ugagaugaag cacuguagcu c                                        21

<210> SEQ ID NO 25
<211> LENGTH: 22
<212> TYPE: RNA
<213> ORGANISM: Homo sapiens

<400> SEQUENCE: 25
aaaguucuga gacacuccga cu                                       22

<210> SEQ ID NO 26
<211> LENGTH: 22
<212> TYPE: RNA
<213> ORGANISM: Homo sapiens

<400> SEQUENCE: 26
ucagugcacu acagaacuuu gu                                       22

<210> SEQ ID NO 27
<211> LENGTH: 22
<212> TYPE: RNA
<213> ORGANISM: Homo sapiens

<400> SEQUENCE: 27
aaguucuguu auacacucag gc                                       22

<210> SEQ ID NO 28
<211> LENGTH: 22
<212> TYPE: RNA
<213> ORGANISM: Homo sapiens

<400> SEQUENCE: 28
ucagugcauc acagaacuuu gu                                       22

<210> SEQ ID NO 29
<211> LENGTH: 22
<212> TYPE: RNA
<213> ORGANISM: Homo sapiens

<400> SEQUENCE: 29
uacggugagc cugucauuau uc                                       22

<210> SEQ ID NO 30
<211> LENGTH: 22
<212> TYPE: RNA
<213> ORGANISM: Homo sapiens

<400> SEQUENCE: 30
aucaugaugg gcuccucggu gu                                       22

<210> SEQ ID NO 31
<211> LENGTH: 22
<212> TYPE: RNA
<213> ORGANISM: Homo sapiens

<400> SEQUENCE: 31
guuguuuuag ugaucagaag gu                                       22

<210> SEQ ID NO 32
<211> LENGTH: 23
<212> TYPE: RNA
```

```
<213> ORGANISM: Homo sapiens

<400> SEQUENCE: 32
acaguguauc ucgaagucuu cca                                              23

<210> SEQ ID NO 33
<211> LENGTH: 23
<212> TYPE: RNA
<213> ORGANISM: Mus musculus

<400> SEQUENCE: 33
acaguguguu ucaaagucuu cca                                              23

<210> SEQ ID NO 34
<211> LENGTH: 23
<212> TYPE: RNA
<213> ORGANISM: Rattus norvegicus

<400> SEQUENCE: 34
acaguguauu ucaaagucuu cca                                              23

<210> SEQ ID NO 35
<211> LENGTH: 23
<212> TYPE: RNA
<213> ORGANISM: Canis familiaris

<400> SEQUENCE: 35
acaguguauu uuaaacucuu cca                                              23

<210> SEQ ID NO 36
<211> LENGTH: 23
<212> TYPE: RNA
<213> ORGANISM: Gallus gallus

<400> SEQUENCE: 36
acaguguauu uugaagucuu cca                                              23
```

RNA TARGETING IN ALPHA-SYNUCLEINOPATHIES

This application claims priority to U.S. Provisional Application No. 61/215,556, filed May 6, 2009, the contents of which are hereby incorporated by reference in its entirety.

FIELD OF USE

This invention relates to therapies and assays to screen for small molecules that can have therapeutic use in the control of neurodegenerative diseases such as Parkinson's and other alpha-synucleinopathies.

BACKGROUND

Neurodegenerative diseases such as Parkinson's disease and other alpha-synucleinopathies are chronic debilitating disorders for which no cure is known.

Parkinson's disease (PD) is a common neurodegenerative disorder that affects 1% of the population over 65. It is characterized by disabling motor abnormalities including tremor, slow movements, rigidity and poor balance. These impairments stem from the progressive loss of dopaminergic neurons in the substantia nigra pars compacta. Eventually, large percentages of patients develop dementia and hallucinations when the pathology involves other brain regions as well. Although the majority of Parkinson cases appear to be sporadic, the disorder runs in families in about 15-20% of the cases. To date, five distinct genes have been identified to cause PD including α-synuclein, parkin, dj-1, pink1 and lrrk2 1. Understanding how mutations in these genes cause neurodegeneration is crucial in the development of new treatments that might slow or stop the disease progression. Thus there remains a need for new treatments for the disease progression and for assays to help identify agents for such treatment.

Accumulating evidence indicates that increased levels of the protein α-synuclein is deleterious to neurons and can lead to such disorders including Parkinson's disease. This invention relates to the identification of a new mechanism by which the expression of this protein can be down-regulated by targeting its RNA. The study of and control of this heretofore unrecognized mechanism can be used as a therapeutic target and to screen small molecules that can mimic the effect for therapeutic intent in these diseases.

SUMMARY OF THE INVENTION

The present invention is related to treatments of neurodegenerative diseases associated with excess α-synuclein (α-Syn) expression via miRNAs, and mimics thereof, which suppress α-synuclein expression and/or inhibit α-synuclein-mediated cell death.

Therefore, in certain embodiments, the present invention is directed to a method for the treatment of a neurodegenerative disease associated with increased levels of α-synuclein comprising administering an effective amount of a substance that suppresses α-synuclein expression to a patient in need thereof.

In other embodiments, the present invention is directed to a method for treating a neurodegenerative disease comprising administering an effective amount of a miRNA or a mimic thereof to a patient in need thereof, wherein the miRNA is selected from the group consisting of miRNA-7, miRNA-153, miRNA-223, miRNA-504, miRNA-920, miRNA-34b, miRNA-374, miRNA-129, miRNA-144, miRNA-143, miRNA-148, and miRNA-433.

In preferred embodiments, the neurodegenerative diseases include Parkinson's disease, dementia with Lewy bodies, multiple system atrophy, and other α-synucleinopathies.

In certain embodiments, the present invention is directed to a method for suppressing α-synuclein expression in a subject comprising administering an effective amount of miRNA or a mimic thereof to a subject.

In yet other embodiments, the present invention is directed to a method for inhibiting α-synuclein-mediated cell death in a subject comprising administering an effective amount of a miRNA or a mimic thereof to a subject.

In certain embodiments, the present invention is directed to a composition comprising a miRNA or mimic thereof which suppresses α-synuclein expression in a subject or inhibits α-synuclein-mediated cell death in a subject.

As used herein, the phrase "effective amount" means an amount for providing the therapeutic effect of the composition or substance being administered.

As used herein, the term "mimic" refers to a composition which, although structurally different, exhibits the same mechanism of action or effect of another composition or substance, thereby producing the same or essentially the same end result.

As used herein, the term "patient" refers to a mammal, human or otherwise, suffering from a disease or condition.

As used herein, the term "subject" refers to organisms to be treated by the methods of the present invention. Such organisms can be any type of organism, e.g., single-cell organisms to more complex organisms such as eukaryotes (e.g., rodents, bovines, porcines, canines, felines, and the like). For the purposes of this application, the term "subject" also includes any substance derived from an organism, for example, a subject may be cellular tissue derived from a mammal used in in-vitro testing.

As used herein the term "treating" includes abrogating, substantially inhibiting, slowing or reversing the progression of a condition, substantially ameliorating clinical or aesthetical symptoms of a condition, substantially preventing the appearance of clinical or aesthetical symptoms of a condition, and protecting from harmful or annoying stimuli.

It must be noted that as used herein and in the appended claims, the singular forms "a", "and", and "the" include plural references unless the context clearly dictates otherwise.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

BRIEF DESCRIPTION OF THE FIGURES

The invention is more fully disclosed below in conjunction with the attached Figures wherein:

FIGS. 1A, 1B, 1C and 1D show miR-7 regulates endogenous α-Syn levels.

FIG. 1A depicts a schematic diagram of human α-Syn mRNA containing the predicted conserved target site of miR-7.

FIG. 1B depicts a Western blot using SYN-1 antibody to show miR-7 reduces the level of endogenous α-Syn in HEK293T cells.

FIG. 1C depicts mean levels of α-Syn protein in FIG. 1B calculated from three independent experiments.

FIG. 1D depicts quantitative RT-PCR analysis of α-Syn and EGFR mRNA expression in HEK293T cells.

FIG. 2A depicts schematic diagrams of human α-Syn 3'-UTR luciferase constructs showing wild-type and mutant (α-Syn-3'-mUTR) miR-7 target sequences.

FIG. 2B depicts the level of luciferase activities of HEK293T cells transfected with luciferase constructs shown in FIG. 2A and 40 nM miR-7 and harvested 24 h later.

FIG. 2C depicts the level of luciferase activities of HEK293T cells transfected with pri-miR-7-2.

FIGS. 3A, 3B and 3C show miR-7 inhibitor increases α-Syn protein level.

FIG. 3A shows a representative Western blot using SYN-1 antibody of SH-SY5Y cells transfected with the indicated concentrations of anti-miR-7 inhibitor (2'-O-methyl) and harvested 48 h later.

FIG. 3B depicts the mean amount of α-Syn measured from three independent experiments normalized to β-actin.

FIG. 3C depicts the levels of luciferase activity of SH-SY5Y cells transfected with luciferase constructs and 50 nM 2'-Omethyl inhibitor of miR-7 and harvested 24 h later.

FIG. 4A depicts a schematic diagram of A53T mutant α-Syn construct with or without its 3'-UTR.

FIG. 4B depicts a representative Western blot using LB509 antibody of mouse neuroblastoma NS20Y cells transfected with constructs shown in FIG. 4A along with 50 nM miR-7 or control (scrambled miR sequence).

FIG. 4C depicts the average relative level of α-Syn (A53T) measured from three independent experiments normalized to EGFP expression.

FIG. 4D depicts chymotryptic proteasome activity measured in NS20Y cells transfected and harvested 24 h later.

FIG. 4E depicts the % of cell death from NS20Y cells transfected with α-Syn (A53T) constructs in the absence or presence of miR-7.

DETAILED DESCRIPTION

Figure 1B:
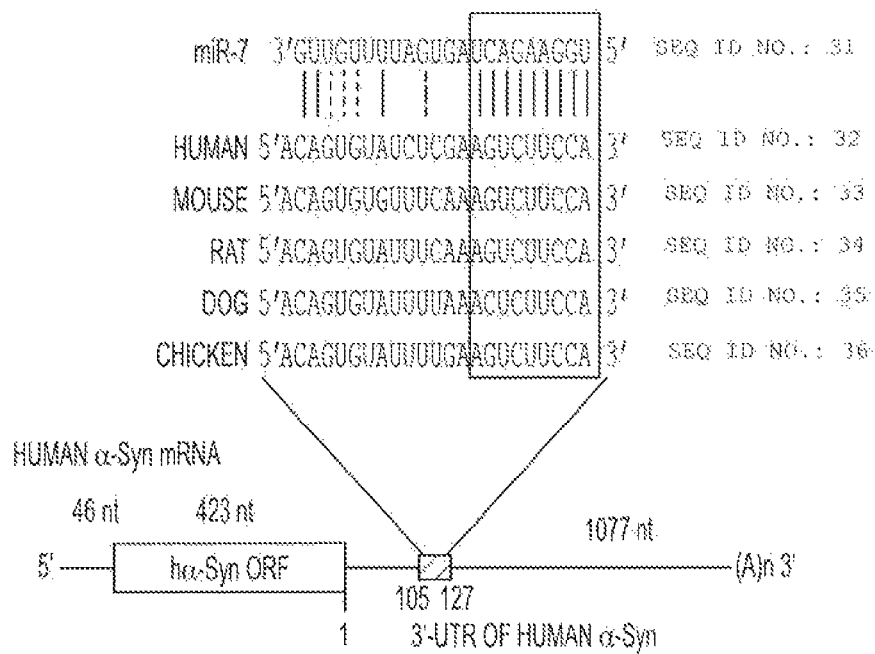
Figure 1B:
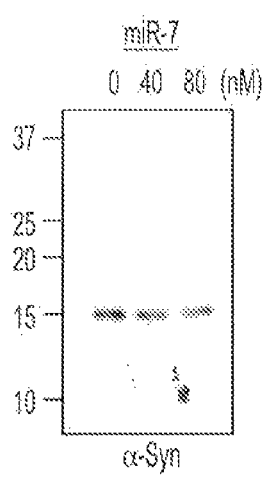
Figure 1C:
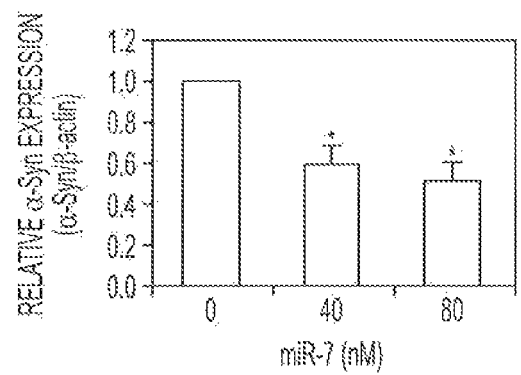
Figure 1D:
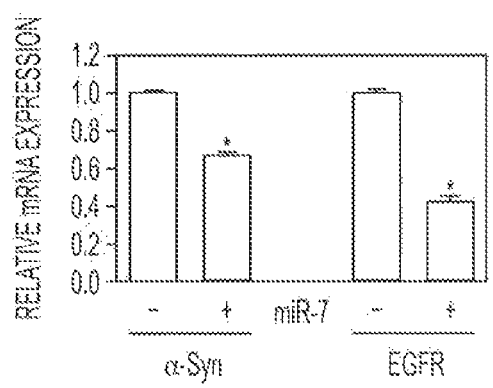

α-Synuclein (α-Syn) is a key player in the pathogenesis of PD based on genetic, neuropathologic and cellular/molecular lines of evidence. In addition to point mutations linked to dominantly inherited PD, mounting evidence suggests that elevated levels of α-Syn are deleterious to dopaminergic neurons. Individuals with multiplication of this gene locus develop PD with an earlier onset age and increasing severity associated with dementia in a gene dosage dependent manner, transgenic mice, drosophila and C. elegans over-expressing α-Syn manifest phenotypic changes reminiscent of the disease, and engineered cultured cells are made vulnerable by this protein. In addition, a large-scale analysis in patients with PD and controls showed that variability in the α-Syn promoter region, which results in its up-regulation, is associated with an increased risk of PD. Besides these compelling data, postmortem investigations of PD and other α-synucleinopathies have demonstrated fibrillar α-Syn aggregates in Lewy bodies and Lewy neurites. An immunization approach to clear the brain of the α-Syn burden has been shown to reduce the neurodegeneration in transgenic mice. Based on the aforementioned evidence, α-Syn over-expression appears to be a common mechanism for the pathogenesis of PD and other α-synucleinopathies.

MicroRNAs (miRNAs) are a class of endogenous 17-24 base-long single-stranded, non-coding RNAs that regulate gene expression in a sequence-specific manner in plants and animals. miRNAs are derived from long precursor transcripts by the action of nucleases Drosha and Dicer, and the resulting mature functional miRNAs bind to their target sequence in the 3' untranslated region (UTR) of mRNA with imperfect complementarity and lead to repression of translation. Recently, miRNAs have been suggested to play important roles in diverse biological phenomena including development, oncogenesis and brain functions. Some miRNAs are specifically expressed and enriched in the brain, and have been associated with memory, neuronal differentiation and synaptic plasticity. The role of miRNAs in neurodegeneration has been suggested in several reports. Interestingly, miR-133b, which is specifically expressed in midbrain dopaminergic neurons and controls their maturation and function through its effect on the homeodomain transcription factor Pitx3, is deficient in PD brains, suggesting that miR-133b is essential for the maintenance of these neurons and could therefore play a role in PD pathogenesis.

It has now been found that miR-7 represses α-Syn expression and inhibits α-Syn-mediated cell death.

Increased α-Syn gene (SNCA) dosage due to locus multiplication leads to autosomal dominantly inherited PD, suggesting that higher concentration of α-Syn protein in neurons is involved in the pathogenesis of PD. In sporadic PD, it is conceivable that various genetic or environmental factors that up-regulate α-Syn expression can be potential culprits as well. Recent evidence suggests that miRNAs regulate a plethora of genes and are involved in many disease states ranging from cancer to neurodegeneration. In the examples which follow, the first experimental evidence for a specific miRNA species that directly represses α-Syn protein levels and protects against α-Syn-mediated cytotoxicity is described.

miR-7, which is a brain-enriched miRNA, binds to the 3'UTR of α-Syn mRNA in a sequence dependent manner and significantly inhibits its translation. GenBank BLAST search revealed that miR-7 is found in human, mouse, rat, zebra fish and fly, suggesting that it regulates biological functions conserved between vertebrates and invertebrate. Antisense inhibition of miR-7 has been found to down-regulate cell growth and increase apoptosis, suggesting that miR-7 has a protective role. The latter finding is consistent with observation that miR-7 suppresses α-Syn mediated cell death. In contrast, miR-7 can also have tumor suppressor-like characteristics in glioblastomas. It potently down-regulates the EGF receptor (EGFR) as well as upstream players of the Akt pathway. Additionally, miR-7 is down-regulated in human glioblastoma tissue relative to surrounding normal brain. The apparent discrepancy between the anti- and pro-cell death activity of miR-7 might reflect the complex regulatory role of this microRNA, requiring additional investigations into its biology in different cellular contexts.

miR-7 is transcribed from three loci in the human genome and one locus of the mouse genome. miR-7-1 is located within an intron of the HNRNPK gene on chromosome 9, which encodes a ribonucleoprotein. Profiling microRNA expression in various tissues has found miR-7 highly expressed in the pituitary gland, presumably because miR-7-3 is transcribed from an intron of pituitary gland-specific factor 1a (PGSF1) gene.

Based on the prediction algorithm of Target Scan v5.1, miRNA-153, miRNA-223, miRNA-504, miRNA-920, miRNA-34b, miRNA-374, miRNA-129, miRNA-144, miRNA-143, miRNA-148, and miRNA-433, based on their similar characteristics to miR-7, will also repress α-Syn expression and inhibit α-Syn-mediated cell death. Some of these target sequences in the 3'-UTR of α-Syn are highly conserved.

The present finding pointing to the importance of the 3'-UTR and miRNA target sites in controlling α-Syn expression also raises the possibility of polymorphisms at these sites contributing to PD susceptibility. Several polymorphisms in the 3'-UTR of the human α-Syn gene are reported in GeneBank but not in the target sites of miR-7 or miR-153. Instead, a polymorphic variation (rs10024743) lies in the potential target site of miR-34b. A polymorphic variation in the miR-433 binding site of the fibroblast growth factor 20 (FGF20) gene was recently reported to confer risk of PD which was attributed to increasing FGF20 levels and indirectly α-Syn expression.

Several studies have implicated miRNAs in brain diseases. For example, a mutation in the target site of miR-189 in the human SLITRK1 gene has been shown to be associated with Tourette's syndrome. In addition, conditional deletion of Dicer in murine post-mitotic Purkinje cells resulted in progressive loss of miRNAs, cerebellar degeneration and ataxia. miRNAs regulate the expression of ataxin1, amyloid precursor protein (APP) and BACE1, and have been suggested to contribute to neurodegenerative disorders. These observations and our present findings raise the possibility that mutations in miR-binding sites or in miR genes themselves can trigger neurodegenerative disease.

Inhibitors of α-Syn expression are attractive therapeutic targets for PD and other αsynucleinopathies. The results shown here provide a new target that can accomplish this objective and potentially slow or halt PD progression.

To that end, the miRNAs described herein, and small molecules which mimic the effects of such miRNAs, may be administered to a subject or patient to treat neurodegenerative diseases associated with excess α-Syn expression. When administered to a subject or patient, the miRNA can be administered as a component of a composition that comprises a pharmaceutically acceptable carrier or excipient. In certain embodiments, the compositions of the invention can be administered by infusion or bolus injection, by absorption through epithelial or mucocutaneous linings (e.g., oral mucosa, rectal, and intestinal mucosa, etc.), by oral administration, and can be administered together with another therapeutic agent. Administration can be systemic or local. Various delivery systems are known, e.g., viral vectors, encapsulation in liposomes, microparticles, microcapsules, capsules, etc., and can be used to administer the composition comprising miRNA described herein or mimic thereof.

Methods of administration include but are not limited to intradermal, intramuscular, intraperitoneal, intravenous, subcutaneous, intranasal, epidural, oral, sublingual, intracerebral, intravaginal, transdermal, rectal, by inhalation, or topical, particularly to the ears, nose, eyes, or skin.

The compositions can optionally comprise a suitable amount of a pharmaceutically acceptable excipient so as to provide the form for proper administration to the subject or patient. Such pharmaceutical excipients can be liquids, such as water and oils, including those of petroleum, animal, vegetable, or synthetic origin, such as peanut oil, soybean oil, mineral oil, sesame oil and the like. The pharmaceutical excipients can be saline, gum acacia, gelatin, starch paste, talc, keratin, colloidal silica, urea, and the like. In addition, auxiliary, stabilizing, thickening, lubricating, and coloring agents may be used. When administered to a patient, the pharmaceutically acceptable excipients are, in certain embodiments, sterile. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like.

The following examples are set forth to assist in understanding the invention and should not, of course, be construed as specifically limiting the invention described and claimed herein. Such variations of the invention, including the substitution of all equivalents now known or later developed, which would be within the purview of those skilled in the art, and changes in formulation or minor changes in experimental design, are to be considered to fall within the scope of the invention incorporated herein.

EXAMPLES

Example 1

Identification of miR-7 as a Regulator of α-Syn Expression

The human α-Syn gene has a 3' UTR that is more than twice as long as its open reading frame (ORF), raising the possibility that it might contain post-transcriptional regulatory elements that would control its protein level. To search for miRNA(s) that might regulate human α-Syn expression, we utilized public prediction algorithms found in several web sites, such as miRbase (http://microrna.sanger.ac.uk/sequences/), Targetscan (http://www.targetscan.org/), Pictar (http://pictar.mdc-berlin.de/), and miRanda (http://www.microrna.org/microrna/home.do). A number of miRNA target sequences were predicted and described above. miRNA-7 (miR-7) was common to all predictions. Expression of miR-7 was previously verified in human, mouse and zebra fish and found to be especially enriched in the brain. FIGS. 1A-D show miRNA-7 regulates endogenous α-Syn levels. The seed match between miR-7 and α-Syn 3'-UTR is between bases 119 and 127, and this target region is conserved in human, mouse, rat, dog and chicken (FIG. 1A). The free energy required for the interaction between miR-7 and its cognate α-Syn 3'-UTR binding site is −22.7 kcal/mol based on the Pictar prediction.

To test the role of miR-7 in regulating α-Syn protein expression, HEK293T cells, which express significant amounts of endogenous α-Syn, were transfected with pre-miR-7 duplex at two concentrations and harvested 48 h later. miR-7 reduced α-Syn expression dose-dependently: 40 nM miR-7 resulted in 40% reduction of α-Syn expression, and 80 nM miR-7 reduced it by 50% (FIG. 1B,C). Endogenous levels of α-Syn in human dopaminergic neuroblastoma. SH-SY5Y and mouse neuroblastoma NS20Y cells are too low to detect the effect of miR7 (Data not shown).

Next, we investigated the effect of miR-7 on α-Syn mRNA levels by quantitative RTPCR. Transfection of HEK293T cells with 40 nM miR-7 significantly reduced α-Syn mRNA expression by 34% (FIG. 1D), indicating that miR-7 promotes the degradation of this target mRNA. Both mRNA expressions are normalized to GAPDH mRNA, and are shown as a ratio to control (scrambled miR-7 sequence)-transfected cells. Experiments were done in triplicates. Data are shown as means±S.D. *P<0.01 for difference between control and miR-7 treated samples. As positive control in this experiment, miR-7 also reduced Epidermal Growth Factor Receptor (EGFR) mRNA expression by 57%, as reported previously.

Repression of α-Syn Expression by miR-7 Requires α-Syn 3'-UTR.

Figure 2A:
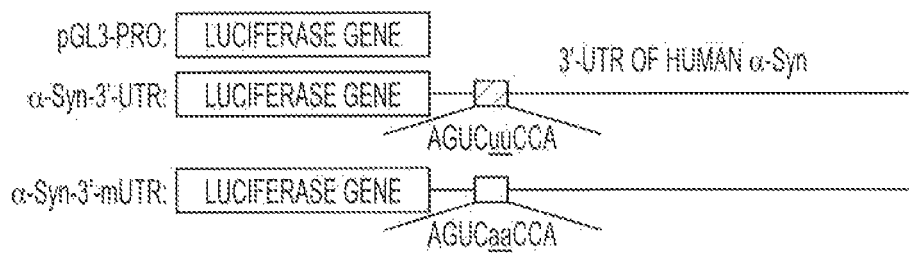
FIGS. 2A, 2B and 2C show miR-7 acts on the 3'-UTR of α-Syn mRNA.
Figure 2B:
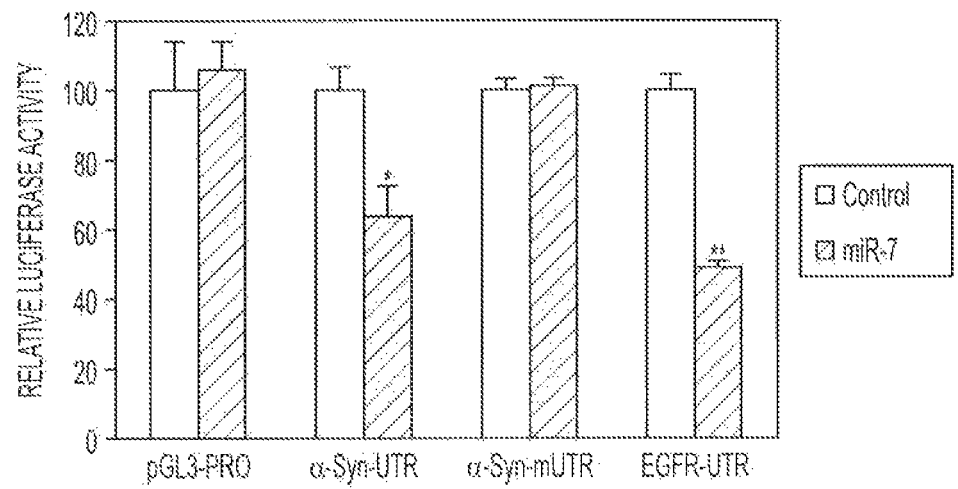
Figure 2C:
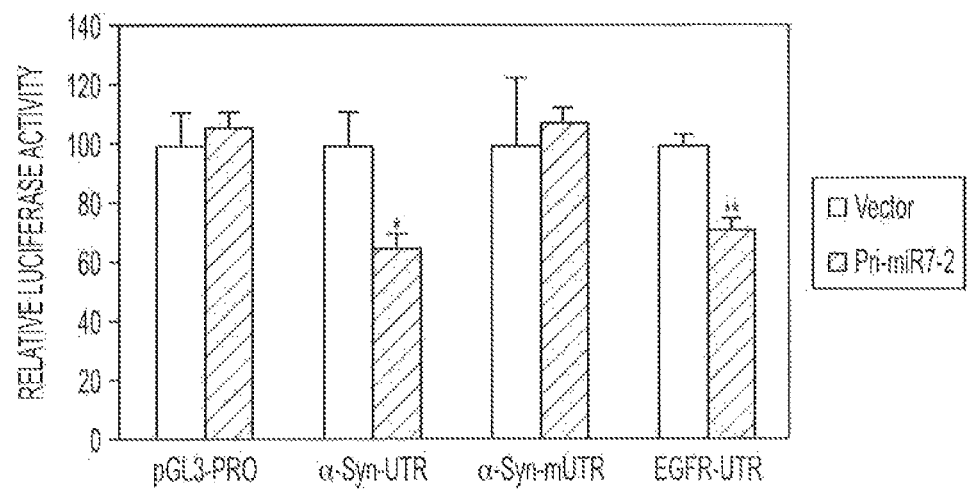

To test if miR-7 directly targets the 3'-UTR of α-Syn, this full-length 3'-UTR was inserted downstream of the firefly luciferase reporter gene (FIG. 2A) and co-transfected with duplex miR-7 into HEK293T cells. miR-7 significantly decreased luciferase activity from α-Syn-3'-UTR construct in a dose-dependent manner, but had no effect on pGL3-pro construct, which lacks α-Syn 3'-UTR (FIG. 2B). As positive control, miR-7 significantly inhibited luciferase activity from EGFR-3'-UTR-containing construct by 50% (FIG. 2B), consistent with previous reports. The effect of miR-7 on the α-Syn 3'-UTR in a luciferase construct was also replicated in SH-SY5Y cells. To confirm that the predicted target sequence of miR-7 in the α-Syn 3'-UTR is functional, this site was mutagenized as shown in FIG. 2A. Notably, miR-7 could not inhibit luciferase activity from the mutagenized α-Syn-3'-UTR construct (FIG. 2B) indicating that the predicted sequence is indeed a genuine binding site for miR-7. Further, we confirmed the effect of miR-7 on α-Syn expression using a pri-miR-7-2 vector expressing miR-7. Transfection of HEK293T cells with pri-miR-7-2 consistently inhibited luciferase activity from constructs having α-Syn-3'-UTR as well as EGFR-3'-UTR but not from α-Syn-3'-UTR mutated at the miR-7 seed sequence (FIG. 2C). This experiment also shows that HEK293T cells can efficiently process pri-miR-7 to mature functional miR-7. *P<0.05, **P<0.01 for difference between control and miR-7-treated samples.

miR-7 Inhibitor Up-Regulates α-Syn Expression.

Anti-miR™ miRNA Inhibitors are chemically modified (2'-O-methyl), single-stranded nucleic acids designed to specifically bind to and inhibit endogenous miRNAs. By using this specific inhibitor against miR-7, we found that endogenous level of α-Syn protein was significantly increased in SHSY5Y cells (FIG. 3A,B). In addition, luciferase activity from the plasmid containing α-Syn-3'-UTR also increased significantly in the presence of miR-7 inhibitor, whereas those from constructs having α-Syn mutant 3'UTR (α-Syn-3'-mUTR) or no 3'-UTR (pGL3-pro) were not affected (FIG. 3C). Once again, as positive control, EGFR-3'-UTR responded by increased expression in the presence of miR-7 inhibitor. These results confirm that miR-7 inhibits α-Syn expression through the 3'-UTR, and further suggest that endogenous miR-7 actively suppresses α-Syn expression in SH-SY5Y cells, which could be blocked by miR-7 inhibitor. *P<0.05, **P<0.01 for difference between control and miR7 inhibitor treated samples.

Figure 4A:
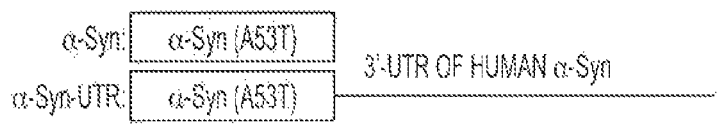
FIGS. 4A, 4B, 4C, 4D and 4E show miR-7-mediated reduction of α-Syn level protects against proteasome impairment and cell death.
Figure 4B:
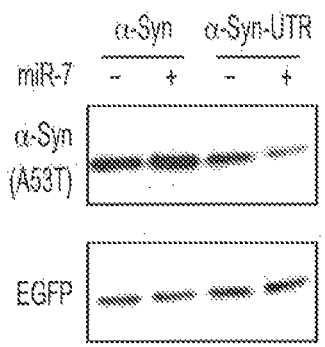
Figure 4C:
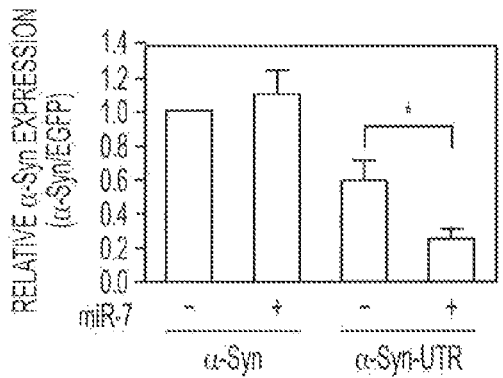
Figure 4D:
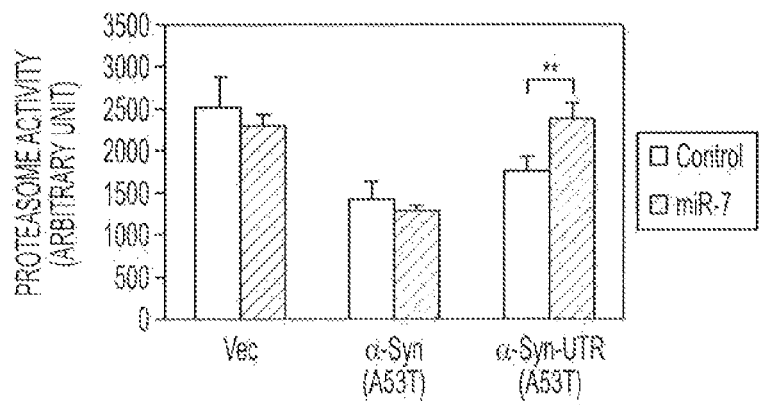

MirR-7 Protects Against α-Syn-Induced Proteasome Inhibition and Cytotoxicity.

α-Syn over-expression and particularly its PD causing A53T mutant increases the susceptibility of cells to oxidative stress, which is a consistent abnormality in the PD brain. Further, the A53T mutant form of α-Syn reportedly impairs proteasome activity. To investigate if miR-7 regulates α-Syn-mediated proteasome inhibition and cytotoxicity, we generated constructs expressing the α-Syn open reading frame harboring the A53T mutation with or without its full length 3'-UTR (FIG. 4A). Cotransfecting miR-7 along with these constructs significantly reduced α-Syn (A53T) expression from the 3'-UTR containing plasmid but not from the construct lacking the 3'UTR (FIG. 4B,C). pEGFP-C1 was used as internal control for normalization of transfection efficiency. Interestingly, even in the absence of exogenous miR-7 transfection, the amount of human α-Syn protein expressed from the construct without 3'-UTR was 2-fold higher than that from the construct with 3'-UTR, suggesting that endogenous mouse miRNA(s) act on the 3'-UTR of this construct. As shown in FIG. 4D, A53T mutant α-Syn expression resulted in inhibition of chymotryptic proteasome activity regardless of the presence of the 3'-UTR, while co-expression of miR-7 significantly recovered this proteasome activity only in the presence of α-Syn 3'-UTR. Cells were also transfected with pSV-β-Gal plasmid as an internal control for transfection efficiency, and proteasome activity values were normalized with β-galactosidase activity. Experiments were done in triplicates. Additionally, miR-7 recovered tryptic and post-acidic proteasome activities inhibited by A53T α-Syn.

Figure 4E:
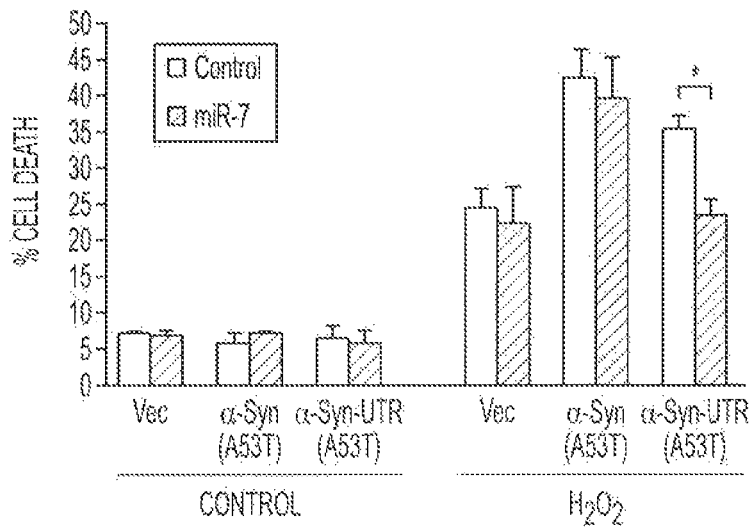

Next, the cytotoxicity of mutant α-Syn was tested. Since NS20Y cells do not manifest toxicity to the mere expression of α-Syn (A53T), they were also challenged with hydrogen peroxide. As expected, A53T α-Syn transfected cells demonstrated increased sensitivity to H2O2 compared to empty vector transfected cells (FIG. 4E). pSV-β-Gal plasmid was used as internal control for normalization of transfection efficiency. After transfection, cells were treated with 200 μM H2O2 for 16 h. Experiments were performed in triplicates and repeated independently three times. *P<0.05, **P<0.005 for difference between control and miR-7-treated samples. Notably, in the presence of miR-7 and α-Syn (A53T)-3'-UTR, H2O2-induced cell death was significantly reduced down to the toxicity seen with empty vector transfected cells (FIG. 4E). However, miR-7 did not suppress H2O2-induced cell death in α-Syn (A53T) expressing cells lacking the 3'-UTR or in empty vector transfected cells. Thus, miR-7 completely protects against A53T mutant α-Syn mediated susceptibility to H2O2 in an α-Syn 3'-UTR dependent manner. Taken together, these results indicate that miR-7 inhibits α-Syn expression and thereby protects against α-Syn-mediated proteasome impairment and susceptibility to oxidative stress.

miR-7 Expression in the Mouse Brain.

Figure 5:
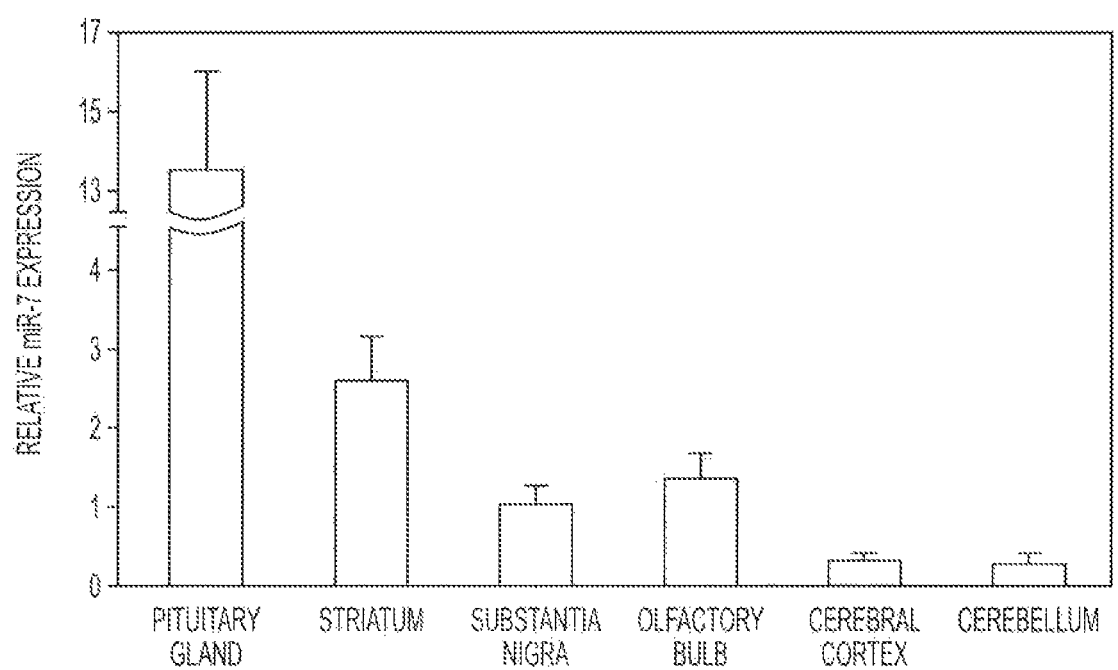
FIG. 5 depicts the relative miR-7 expression in the mouse brain.

Nigral dopaminergic neurons are vulnerable in PD where accumulated α-Syn might cause toxicity. To study the possibility that α-Syn expression in the substantia nigra could be regulated by miR-7, we investigated the level of miR-7 in this and several other regions of the mouse brain by qRT-PCR analysis (FIG. 5). Total RNA samples isolated from brain regions were used for qRT-PCR analysis of miR-7. Amounts are calculated relative to the level in substantia nigra.

As reported, miR-7 expression is highest in the pituitary gland, validating the quality and specificity of this experiment. Interestingly, the substantia nigra, striatum (where nigral dopaminergic nerve terminals project) and olfactory bulb, which are neural systems affected in PD, have relatively higher miR-7 levels compared to the cerebral cortex and cerebellum, raising the possibility that dysregulation of miR-7 in these regions might relate to PD pathogenesis.

Materials and Methods Cell Culture, Transfection and Luciferase Assay.

Human embryonic kidney cell line HEK293T and human neuroblastoma cell line SH-SY5Y were obtained from American Type Culture Collection (ATCC), and mouse neuroblastoma cell line NS20Y was a kind gift from Dr. Marshall Nirenberg (NHLBI, NIH, Bethesda, Md.). All cells were maintained in Dulbecco's modified Eagle's medium (DMEM) containing 10% fetal bovine serum. Pre-miRNA-7 and miRNA-7 inhibitor were purchased from Ambion. Transfections were performed using Lipofectamine 2000 reagent (Invitrogen) according to the supplier's instructions. For luciferase assay, cells were co-transfected with luciferase reporter constructs and internal control construct pSV-β-galactosidase in the absence or presence of miR-7 or pre-miR-7 at the indicated concentrations. After cell lysis, luciferase activity was measured with Steady-Glo Luciferase Assay System (Promega) using Luminometer (Victor2, Perkin Elmer). β-Galactosidase activity was measured with the β-Galactosidase Enzyme Assay System (Promega) and used to normalize luciferase activity. Experiments were performed in triplicates.

Plasmids.

3'-UTR containing reporter plasmids were constructed by inserting the human α-Syn 3'-UTR into the XbaI site located downstream of the luciferase gene in the pGL3 promoter plasmid (Promega), and named α-Syn-3'-UTR. In addition, this 3'-UTR was inserted downstream of human wild-type or A53T mutant α-Syn coding sequence. α-Syn 3'-UTR was amplified from human adult brain cDNA library (Invitrogen) with primers 5'-CTCTAGAGAAATATCTTTGCTCCCA-GTT-3' and 5'CTCTAGACATGGTCGAATATTATTTATT-GTC-3', and cloned into pCR2.1-TOPO plasmid (Invitrogen) before subcloning into pGL3 promoter plasmid and α-Syn expressing plasmids. The plasmid α-Syn-mUTR containing mutation of the miR-7 target site in the α-Syn 3'-UTR was created using the QuikChange site-directed mutagenesis kit (Stratagene) with primers 5'-TCTC-GAAGTCAACCATCAGCAG-3' and 5'CTGCTGATGGT-TGACTTCGAGA-3', and DNA sequences were confirmed. Control plasmids EGFR containing 3'-UTR of EGF receptor, and pri-miR-7-2 expressing premiR-7-2 with 600 bp flanking sequences, were gifts from Dr. Benjamin Purow (University of Virginia).

Western Blot Analysis.

Cell lysates were analyzed by Western blotting as described previously using mouse monoclonal anti-α-Syn antibodies SYN-1, (BD Transduction Lab) and LB509, (Zymed)), mouse monoclonal β-actin antibody (Sigma) and rabbit polyclonal anti-GFP antibody (Santa Cruz Biotech.). Band densities were quantified using NIH Image J.

Quantitative Real-Time RT-PCR (qRT-PCR).

For qRT-PCR of α-Syn, total RNAs were prepared from cells with TRIZOL reagent (GibCo BRL) according to the manufacturer's instructions. Reverse transcription reaction was performed with 1 µg of total RNA per 20 µl reaction. Real-time PCR was performed in triplicates with Taqman PCR Mix (Applied Biosystems Inc., Foster City, Calif.) in the ABI's 7900HT Fast Real-Time PCR System. All primers were purchased from Applied Biosystems Inc. The level of α-Syn mRNA expression was normalized to GAPDH mRNA. For qRT-PCR of miR-7, brains from 12-week old C57/B6 mice were used to prepare total RNA from various regions with miRCURY™ RNA isolation kit (Exiqon) according to the manufacturer's protocol. Reverse transcription was done with miRCURY LNA™ first-strand cDNA kit (Exiqon) and qRT-PCR was performed with miRCURY LNA™ miR-7 primer set (Exiqon) using miRCURY LNA™ SYBR Green master mix (Exiqon) according to manufacturer's instruction.

Proteasome Activity Assay.

Cells were lysed in a buffer containing 50 mM Tris-HCl (pH 8.0), 1 mM ATP, 10% glycerol, 0.1% NP-40, and lysates were centrifuged. Fifty microgram of supernatant protein was used in the assay containing 50 mM Tris-HCl (pH 8.0), 2 mM MgCl2, 1 mM ATP and 100 µM fluorogenic substrates, such as suc-LLVYAMC, z-LLE-AMC and boc-LRR-AMC (Boston Biochem) to measure chymotrypsin-like, trypsin-like and post-acidic activity of proteasome, respectively. Assays were carried out at 37° C. for 20 min. and activities were measured in a fluorometer (Victor2, Perkin Elmer) with 380 nm excitation and 460 nm emission filters. Background levels of fluorescence were determined using lysates incubated with proteasome inhibitor MG-132 (10 µM) for 30 min prior to adding the fluorogenic substrate.

Cell Death Assay.

NS20Y cells transfected with α-Syn-expressing constructs in the absence or presence of miR-7 were exposed to H2O2, and cell death was assessed by lactate dehydrogenase (LDH) Cytotoxicity Detection Kit (Roche Molecular Biochemicals) as described previously.

Statistical Analysis.

Statistical significance between control and experimental values was determined using Student's t test (paired, two-tailed). All data are expressed as mean±standard deviations (S.D.).

Example 2

In Vivo Validation of the Role of Specific microRNAs in Protecting Neurons

To validate the ability of miR-7 and other microRNAs that have the potential to down-regulate α-synuclein expression in the brain, highly efficient lentiviral vectors have been generated that express miR-7 and a scrambled negative control sequence and injected stereotaxically in the substantia nigra of wild-type mice unilaterally. The amount of miR-7 expression as well as the amount of α-synuclein miRNA expression will be measured by real time PCR and α-synuclein protein expression will be assessed by Western blotting. It is expected that α-Synuclein expression will be decreased in microRNA injected brains but not in scrambled sequence injected samples. This paradigm will also be employed to assess the ability of this treatment to protect against the dopaminergic neurotoxin MPTP commonly used to model Parkinson's disease in laboratory animals. In alternative experiments, we will use adeno-associated virus as an alternative vector to deliver microRNAs.

Infection into Mouse Brain.

Lentiviral particle mixture was injected into right lateral substantia nigra of 8 week old C57/BL mice. After anesthesia, the mice were placed in a stereotaxic frame. After placing mice in the stereotaxic frame, 2 µl of highly concentrated viral particles were injected into the nigra (coordinates: AP −3.3 mm, ML −1.2 mm, DV −4.6 mm from bregma) over 5 min. After injection, the needle was left in place for 10 min.

Animals will be sacrificed at 3 different time points, 3 weeks, 8 months and 20 weeks to assess α-Syn mRNA expression by real time-PCR and protein expression by Western blot analysis.

Effect of miRNA on MPTP-Intoxicated Model.

MPTP impairs mitochondrial complex I activity, depletes ATP and leads to oxidative stress. It has been used extensively to produce a toxic model of Parkinson's disease. Since the miRNA species identified by our studies are expected to be protective, we hypothesize that miRNA over-expression also protects against MPTP-induced toxicity in mice. To do this, eight-week old mice will be infected with lenti-LemiR (control) or lenti-miRNA. After two weeks, MPTP (30 mg/kg) will be administered intraperitoneally to animals, once daily for five consecutive days, and will be sacrificed 14 days after the final injection. Control mice will receive saline only. Six to eight mice will comprise each group. Substantia nigra will be dissected quickly and α-synuclein expression will be compared by Western blot analysis. We will check the dopaminergic neuron degeneration in substantia nigra. We expect that miRNA expression spares dopaminergic neurons from MPTP-induced toxicity in mice. Outcome measures will include immunohistochemistry and cell counting as well as striatal dopamine and tyrosine hydroxylase content.

Alternative strategies may also be employed including using AAV vector and evaluate animals at different time points.

Generation of rAAV-miR-7.

Viral vectors harboring pri-miR-7 cDNA sequence (using Sanger miRbase database) will be constructed with AAV vector. Plasmids will be constructed with a cassette containing chicken β-actin-promoter/cytomegalovirus enhancer (CAG promoter) that gives high expression in neuronal cells. As a negative control, we will clone scrambled sequence that does not inhibit any gene expression into this viral vector. To monitor miR-7 expression easily in the mouse brain, we will insert Internal Ribosome Entry Sequence (IRES)-GFP expression unit downstream of miR-7 cDNA, thereby miR-7 and GFP will be expressed bicistronically from a single mRNA. Subsequently, the plasmid DNA, pAAV-miR-7, or pAAV-scramble will be co-transfected with plasmids pHelper and Pack2/1 into HEK293T cells using a standard calcium phosphate method, and 48 hours post-transfection the virus will be harvested. Briefly, crude rAAV supernatants obtained by repeated freeze/thaw cycles will be processed for gradient ultracentrifugation. The fractions containing high titer rAAV will be collected and used for injecting animals. The number of rAAV genome copies will be semi-quantified by PCR within the CMV promoter region using primers 5'-GACGTCAATAATGACGTATG-3' and 5'-GGTAATAGCGATGACTAATACG-3'. Final titers will be set to $6\text{-}10\times10^{11}$ genome copies/ml.

In Vitro Infection of rAAV-miR-7.

After generating rAAV-miR-7, we will first test its effectiveness by infecting HEK293T cells, which we have used successfully to study the effect of miR-7 on α-Syn expression. We anticipate to detect increased miR-7 and decreased α-Synuclein expression in GFP-positive rAAV-miR-7-infected cells but not in negative control rAAV-scramble-infected cells. For this experiment, in situ hybridization will be employed to detect miR-7, and immunocytochemical staining will be performed to detect α-Syn, as we reported previously. If infection efficiency approaches nearly 100%, we will check the level of miR-7 by qRT-PCR and α-Syn by Western blot. Subsequently, rAAV-miR-7 with verified effectiveness in vitro will be used for the mouse experiments.

rAAV-miR-7 Gene Transfer into Mouse Brain.

We will inject rAAV-miR-7 or rAAV-scramble into the right lateral substantia nigra. For these experiments, we will use 8 week-old C57/BL mice. All stereotaxic surgical procedures are performed aseptically under anesthesia with ketamine and xylazine. After placing mice in the stereotaxic frame, 2 μl of highly concentrated viral particles will be injected into the nigra (coordinates: AP −3.3 mm, ML −1.2 mm, DV −4.6 mm from bregma) over 5 min. After injection, the needle will be left in place for 10 min.

Although a number of factors including capsid serotype and promoter influence transduction efficiency, most data indicate that transduction may increase during the first two months. Another consideration is the duration of miR-7 expression after a single infection. Therefore, we will sacrifice the animals at 3 different time points, 3 weeks, 8 weeks and 20 weeks to assess the following outcome measures: We will first check the transduction efficiency by examining GFP-positive cells in nigral dopaminergic neurons. Staining of 30 μm thick-coronal sections with an antibody against tyrosine hydroxylase (TH; Sigma) will be performed to visualize nigral dopaminergic neurons as red fluorescence. We will determine if the transduced GFP-positive dopaminergic neurons express high-level of miR-7 by in situ hybridization. Because GFP and miR-7 are produced from a single transcript bicistronically, there will be high level of miR-7 expression in GFP-positive cells. We will assess the level of α-Syn expression in GFP-positive nigral dopaminergic neuronal cells. We expect that there will be decreased α-Syn expression in GFP-positive dopaminergic neurons due to the effect of over-expressed miR-7. Immunohistochemistry with an antibody to α-Syn (SYN-1, BD transduction) will be performed to visualize α-Syn expressing cells as red fluorescence. It will be of interest to learn whether injection of rAAV-miR-7 into the nigra results in reduced α-Syn expression in the striatum, a process that would require anterograde transport of mature miR-7 from cell bodies in the nigra to synaptic terminals in the striatum. Expression levels will be compared between injected and contralateral non-injected sides, as well as between rAAV-miR-7 and rAAV-scramble injected animals at 3 different time points mentioned above. We will check the integrity of dopaminergic neurons in substantia nigra and terminals in striatum by immunohistochemistry, in order to determine if rAAV-miR-7 infection per se produces any toxicity to dopaminergic neurons. For this, TUNEL (Terminal transferase dUTP nick end labeling) staining, which is positive in apoptotic cells, will be performed.

Effect of miR-7 in the MPTP-Lesioned Model.

According to our preliminary studies, miR-7 expression is down-regulated in the midbrain of MPTP-lesioned mice. This finding prompts us to test the effect of miR-7 over-expression in this model. Since our data indicate that miR-7 protects cells against α-Syn-mediated toxicity, we hypothesize that over-expressing miR-7 also protects against MPTP-induced toxicity in mice. The mechanism of such protection will either be through down-regulating α-Syn, since α-Syn null mice are reportedly relatively resistant to MPTP, or regulation of other genes. For this experiment, eight-week old mice will be infected with rAAV-miR-7 or rAAV-scramble (control) into the nigra as described above. After 1 week, 6 weeks and 18 weeks, MPTP (30 mg/kg) or saline will be administered intraperitoneally once daily for five consecutive days, and animals will be sacrificed 14 days after the final injection. We will assess the degeneration of nigral dopaminergic neurons and striatal nerve terminals. We expect that the degree of nigral TH positive neuron loss and striatal dopamine depletion following MPTP administration will be moderated in rAAV-miR-7-infected mice compared to rAAV-scramble-infected animals. Nigral dopaminergic neuron degeneration will be assessed by cell counting using unbiased stereology. Density of dopaminergic neuron terminals in the striatum will be assessed by TH staining and ELISA. In addition, we will measure dopamine content in striatal tissues by HPLC with an electrochemical detector.

These outcome measures will be compared with the contralateral uninjected side as well. We expect that over-expressing miR-7 protects dopaminergic neurons from MPTP-induced toxicity in mice. Throughout the proposed studies, statistical significance between control and experimental groups will be determined by Analysis of Variance for each time point and a significance level of $p<0.05$.

The invention claimed is:

1. A method for decreasing the expression of α-synuclein in a patient in need thereof comprising administering to said patient an effective amount of a composition comprising miRNA-153 (SEQ ID NOs. 3-4).

2. The method of claim 1, wherein the composition comprising miRNA-153 is administered through a delivery system, and wherein the delivery system comprises at least one of a viral vector, a liposome, a microparticle, capsules, and combinations thereof.

3. The method of claim 2, wherein the delivery system comprises a viral vector.

4. The method of claim 1, wherein the patient suffers from Parkinson's disease, dementia with Lewy bodies, or multiple system atrophy.

5. The method of claim 4, wherein the composition comprising miRNA-153 is administered through a delivery system, and wherein the delivery system comprises at least one of a viral vector, a liposome, a microparticle, capsules, and combinations thereof.

6. The method of claim 5, wherein the delivery system comprises a viral vector.

7. A method for treating Parkinson's disease, dementia with Lewy bodies, or multiple system atrophy, in a patient in need thereof comprising administering to said patient an effective amount of a composition comprising miRNA-153 (SEQ ID NOs. 3-4).

8. The method of claim 7, wherein the composition comprising miRNA-153 is administered through a delivery system, and wherein the delivery system comprises at least one of a viral vector, a liposome, a microparticle, capsules, and combinations thereof.

9. The method of claim 8, wherein the delivery system comprises a viral vector.

* * * * *